US012782353B2

(12) United States Patent
Matscheko et al.

(10) Patent No.: US 12,782,353 B2
(45) Date of Patent: Nov. 3, 2026

(54) CELL IMMOBILIZATION IN FLUID AT HIGH FLOW VELOCITIES

(71) Applicant: DYNAMIC BIOSENSORS GMBH, Martinsried/Planegg (DE)

(72) Inventors: Nena Matscheko, Munich (DE); Hanna Müller-Landau, Munich (DE); Ulrich Rant, Munich (DE); Sina Reede, Bremen (DE); Michael Vellekoop, Bremen (DE); Frieder Lucklum, Naerum (DK); Stefanie Mak-Lucas, Munich (DE); Agnes Marszal, Munich (DE)

(73) Assignee: DYNAMIC BIOSENSORS GMBH, Martinsried/Planegg (DE)

( * ) Notice: Subject to any disclaimer, the term of this patent is extended or adjusted under 35 U.S.C. 154(b) by 662 days.

(21) Appl. No.: 18/728,404

(22) PCT Filed: May 26, 2021

(86) PCT No.: PCT/EP2021/064126

§ 371 (c)(1),
(2) Date: Jul. 11, 2024

(87) PCT Pub. No.: WO2021/239855

PCT Pub. Date: Dec. 2, 2021

(65) Prior Publication Data

US 2025/0102505 A1 Mar. 27, 2025

(30) Foreign Application Priority Data

May 26, 2020 (EP) .................................... 20176518

(51) Int. Cl.

| | |
|---|---|
| ***G01N 33/569*** | (2006.01) |
| ***B01L 3/00*** | (2006.01) |
| ***G01N 33/543*** | (2006.01) |

(52) U.S. Cl.

CPC ...... *G01N 33/569* (2013.01); *B01L 3/502761* (2013.01); *G01N 33/54386* (2013.01); *B01L 2200/0652* (2013.01); *B01L 2300/0877* (2013.01); *G01N 2500/10* (2013.01)

(58) Field of Classification Search
None
See application file for complete search history.

(56) References Cited

U.S. PATENT DOCUMENTS

| | | | | |
|---|---|---|---|---|
| 2013/0052653 | A1 | 2/2013 | Stein et al. | |
| 2013/0273053 | A1* | 10/2013 | Schwaeble ............. | C07K 16/40 424/139.1 |
| 2019/0145980 | A1* | 5/2019 | Kang ................. | G01N 33/5759 424/277.1 |
| 2019/0374947 | A1* | 12/2019 | Shrivastava ...... | B01L 3/502715 |

FOREIGN PATENT DOCUMENTS

| | | |
|---|---|---|
| EP | 4158339 B1 * | 10/2025 |

OTHER PUBLICATIONS

The Office of Earlier Examination Listings of Claims dated Jul. 24, 2023 and May 17, 2024.*
European Search Report issued in European Application No. 20176518, mailed Oct. 6, 2020.
International search Report issued in International Application No. PCT/EP2021/064126, mailed Jul. 14, 2021.
Kwon, Donguk et al., "A Nanowire-Integrated Microfluidic Device for Hydrodynamic Trapping and Anchoring of Bacterial Cells," MEMS 2014, San Francisco, CA, USA, Jan. 26-30, 2014, pp. 246-249.

* cited by examiner

*Primary Examiner* — Ann Montgomery
(74) *Attorney, Agent, or Firm* — Bookoff McAndrews, PLLC

(57) ABSTRACT

The present invention relates to methods for the individual immobilization of one or more cells under fluid flow conditions, in the context of a bioassay, comprising for each cell the step of trapping said cell in a reticular structure that is arranged in a microfluidic channel of a microfluidic device in a direction that is perpendicular to the direction of fluid flow. Further, the present invention relates to respective bioassays comprising the step of individually immobilizing one or more cells under fluid flow conditions according to said methods, e.g. assays for determining the kinetics of the binding of a ligand to the immobilized cells. Furthermore, the present invention relates to respective microfluidic devices.

18 Claims, 6 Drawing Sheets

CELL IMMOBILIZATION IN FLUID AT HIGH FLOW VELOCITIES

Figure 1A:
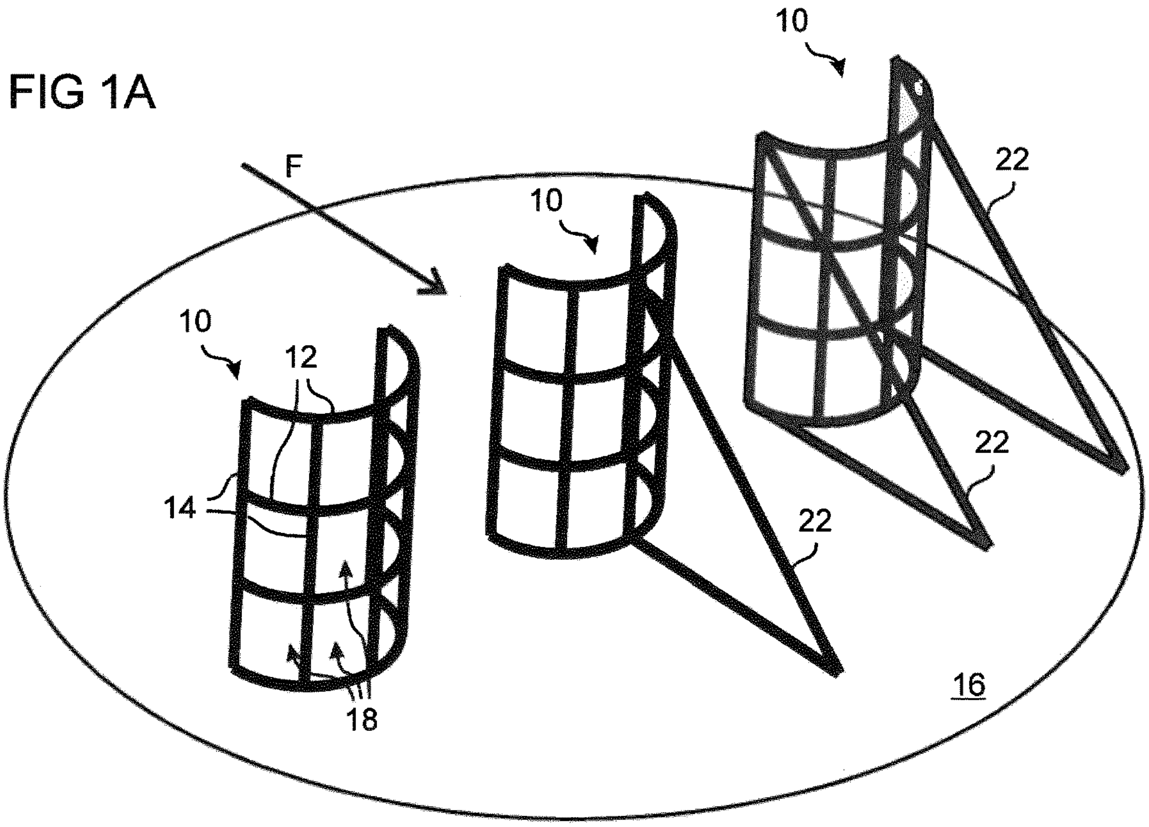

The present invention relates to methods for a locally predetermined immobilization of one or more (e.g. single) cells under fluid flow conditions, in the context of a bioassay (biological assay), comprising for each (single) cell the step of trapping said cell in a reticular structure that is arranged in a microfluidic channel of a microfluidic device and extends in the directions transverse to a direction of fluid flow. Further, the present invention relates to respective bioassays comprising the step of (individually) immobilizing one or more (single) cells under fluid flow conditions according to said methods, e.g. assays for determining the kinetics of the binding of a ligand to the immobilized (single) cells. Furthermore, the present invention relates to respective microfluidic devices.

Major parameters of drugs and their performance are their likelihood to interact with the target (association rate) and the rate at which the complex will fall apart again (dissociation rate). This information about a molecular complex goes far beyond a general binding confirmation and leads towards pharmacokinetics in patients.

Kinetic parameters are classically determined in vitro with a purified target of the drug, e.g. by microfluidic biosensor instruments. However, it is known that the binding behavior of purified targets differs from targets in their natural setting embedded in cellular structures. The leading class of drugs in development for the treatment of all kinds of diseases, for instance of cancer, are antibodies. Many antibodies are developed to target cell surface markers and differentiate between healthy and abnormal cells.

To characterize the in situ binding kinetics and specificity of potential drugs in an early stage of development, it is desirable to immobilize cells in a microfluidic device. The measurement of interaction kinetics without technical artefacts entails the transport of the analyte (drug) to and from the target in a flow with a flow velocity that is preferably at least several 10 μm per second. Further enhanced analytic precision, however, may only be achieved with even significantly higher flow rates of even more than 1 mm per second.

A high flow rate around the cell ensures maximum supply of analyte and avoids the technical reduction of the measured association and dissociation rates by mass transport limitation. Furthermore, high flow rates are indispensable for the immediate removal of analytes as soon as an unbinding event is taking place, preventing rebinding which would result in apparently slower dissociation rates. The present concentration of e.g. antibodies on the cell surface can be determined by following the fluorescence of a label attached to the antibody via a microscopic setup above the immobilized target.

The immobilization of cells in a microfluidic device has no commercial platform to date. Experimental approaches applied include (i) specific capture via antibodies against cell surface markers; (ii) growing of adherent cells directly on a sensor; (iii) cell fixation; and (iv) mechanical barriers to trap the cells in flow.

Specific antibodies have the disadvantages of only being applicable to very specific cells and a rather low retention potential. It has turned out to be very challenging to make use of high flow velocities, when requiring a reliable and stable localization of the target cells. The same applies to adherent cells grown on the sensor surface, as such cells only resist rather slow fluid flow and are limited to adherent cell types. The fixing of adherent cells after growing them might improve their stability on the sensor. However, only kinetics with very limited flow rates have been published to date, indicating that no higher flow could be applied. Additionally, fixing of cells prevents any live-cell response measurements. Immobilization of cells by a mechanical trap can be applied to both adherent and suspension cell types, broadening the application. To date, polydimethyl-siloxane (PDMS) traps have been structured via soft lithography in microfluidic channels. These traps are large barriers and distort the flow before and after cell loading, reducing the fluid velocity that can be applied directly at the cell to about 50 μm/s. Cell loading and observation has only been published in slow flow rates up to a maximum of about 20 μl/min, which corresponded to fluid velocities of to-digit μm/s up to the low mm/s range, depending on the channel cross sectional area. Other technologies have been applied to cell sorting structures, which reduce the flow around each cell, as well as to cell cages for droplet deposition from the top, i.e., no flow is applied.

To determine kinetic rates of drug candidates as close as possible to the in vivo situation, it is necessary or desirable to measure their interaction with targets in situ, e.g. cell surface markers integrated in the native cellular membrane. From a technical point of view, high flow rates are required or desirable to measure real-time kinetics of molecular interactions in a microfluidic channel.

Accordingly, the technical problem underlying the present invention is the provision of means for reliable immobilization of cells, preferably single/individual cells, in a microfluidic environment under fluid flow conditions at flow velocities that are e.g. suitable for accurate kinetic measurements. The solution to the above technical problem is achieved by the embodiments characterized in the claims.

In particular, in a first aspect, the present invention relates to a method for the individual immobilization of one or more (single) cells under fluid flow conditions, comprising for each (single) cell to be immobilized the step of trapping said cell by means of a cell trapping element, which comprises a reticular structure that is arranged in a microfluidic channel of a microfluidic device and such that it extends in the directions substantially transverse to the direction of a main fluid flow in the microfluidic channel.

The method of the present invention is usually performed in the context of a bioassay, e.g. a bioassay as defined hereinafter. As used herein, the term "individual immobilization" relates to the fact that according to the present invention, preferably one single cell is immobilized or trapped in one reticular structure each, i.e. by a separate cell trapping element. More than one cell can be measured (and compared) in accordance with preferred implementations of the present invention by either capturing the cells in separate cell trapping elements and/or by measuring the cells in the same cell trapping element sequentially. In the latter case, after measurement of a trapped cell, said cell can be released in a controlled manner by reverting the direction of the fluid flow for a short time. And with subsequent forward flow, the next (single) cell can be trapped in the same cell trapping element.

Further, the term "under fluid flow conditions" as used herein is intended to indicate that the method of the present invention is performed, and each (single) cell is immobilized or trapped, hydrodynamically, while a fluid is flowing through the microfluidic channel, where the fluid flow is particularly applied at the location of the trapped cell. In other words, different from some conventional approaches, the present invention does not try to avoid or reduce an effective fluid flow at the location of the cell in order to prevent washing the cell away from its location of immobilization. Instead, the cell is directly exposed to the fluid flow by holding the cell trapped in the reticular structure of the respective cell trapping element, while the reticular structure allows largely unimpeded fluid flow at the location of the trapped cell. According to the present invention, this is achieved by the making use of the specific structure of the cell trapping element applied, wherein the reticular structure is composed of a plurality of struts that define a plurality of windows (openings), which allow fluid to flow through said windows.

Thus, the reticular structure defines a mesh with a mesh size adapted to retain a cell but to support fluid flow directly around the cell and through the windows (openings) in the mesh. In that respect, the windows may at least partially allow fluid flow therethrough even while a cell is trapped (and thereby immobilized) by means of the reticular structure. It turned out that such an arrangement is specifically effective in supporting high flow rates at the location of the immobilized cell without detaching the cell, which was a problem in known immobilization methods. The reticular structure thereby keeps any impact on the fluid flow very low and allows fast buffer exchange around the entire cell. Thereby, the present invention effectively combines good buffer exchange with accurate kinetic rate determination, where in conventional approaches a course tradeoff was required. Specifically, in most conventional approaches a choice was made between good buffer exchange which could easily wash away the cell as well, and very low flow rates and cells sitting in low flow areas which limited the accuracy of kinetic rate determination.

In preferred embodiments, the fluid velocity of the fluid flow at the location of the reticular structure and/or at the location of the trapped cell is set to a value of at least about 1 mm/s, preferably at least about 5 mm/s, more preferably at least about 10 mm/s, even more preferably at least about 50 mm/s, most preferably at least about 0.1 m/s or even at least about 0.5 m/s. Preferably, the fluid velocity at a location of the trapped cell and/or at the location of the reticular structure is specifically set to a value in the range of about 0.07 to about 0.74 m/s.

In a preferred embodiment, the microfluidic channel has cross section transvers to the direction of the (main) fluid flow specifically at the location of the at least one cell trapping element and/or at a center location of the trapped cell such that a volumetric flow rate of the fluid flow is at least about 20 μl/min, more specifically at least about 40 μl/min and preferably in the range from about 40 μl/min to about 3.5 ml/min, more preferably in the range from about 100 μl/min to about 2 ml/min, particularly while applying a fluid velocity according to one of the preferred values described herein. Specifically, the microfluidic channel preferably has a cross section transvers to the direction of the fluid flow in the range of about $0.2 \cdot 10^4$ $\mu m^2$ to about $20 \cdot 10^4$ $\mu m^2$, more specifically in the range of about $1 \cdot 10^4$ $\mu m^2$ to about $5 \cdot 10^4$ $\mu m^2$.

In this context, the term "volumetric flow rate" is defined as the volume of fluid which passes through the microfluidic channel in which the reticular structure(s) is/are arranged per unit time. Further, the term "fluid velocity" (or "flow velocity") is defined as the momentary velocity of an element of fluid at a given location. As used herein, the terms "trapping/trapped" and "immobilizing/immobilized" are used synonymously and relate to the act of retaining one or more cells, preferably a single cell, at a given location in the microfluidic channel under fluid flow conditions by way of the reticular structures arranged in said channel.

In another aspect, the present invention also provides a microfluidic device for the individual immobilization of one or more (single) cells under fluid flow conditions of a bioassay. While the method for individual immobilization of one or more (single) cells as described herein may apply this microfluidic device according to any one of the preferred implementations disclosed herein, the structural and functional details disclosed in connection with the method are preferably also implemented in the microfluidic device. Thus, the microfluidic device comprises a microfluidic channel supporting continuous fluid flow along a fluid flow direction. It further comprises the cell trapping element having the reticular structure and being arranged in the microfluidic channel such that the reticular structure extends in the directions transverse to the fluid flow direction. As already explained in connection with the method for immobilization, the reticular structure is composed of a plurality of struts that define a plurality of windows allowing fluid to flow through said windows, such that (single) cells can be held trapped by the cell trapping element under fluid flow conditions.

In one specific aspect, the present invention relates to a bioassay comprising the step of individually immobilizing one or more (single) cells under fluid flow conditions according to the method of the first aspect of the present invention. Respective bioassays are not particularly limited and include any assay in which the immobilization of (single) cells under fluid flow conditions might be of interest. Such assays include e.g. assays for determining the kinetics of the binding of a ligand to the immobilized (single) cells. By way of example, such assays include studies of the binding kinetics of an antibody to a structure on the surface of the cells, or the binding kinetics of a drug or drug candidate to the cells. Such kinetic binding assays are known in the art. In specific embodiments, respective assays include the detection of a detectable marker, e.g. a fluorescent marker, that is bound to the cells.

In other embodiments, respective bioassays in which a physiological response of the immobilized cells is triggered, and said response, e.g. the release of a certain factor, is measured either directly on the cells or with the help of a biosensor in the immediate vicinity of the immobilized cells, or a biosensor lying downstream of the immobilized cells. The bioassay may assess and quantify cell viability, cell morphology, internalization of cell surface structure, release of vesicles and/or molecules of cellular origin, intercellular signaling, and/or changes in cellular metabolism and/or enzymatic activity in response to a stimulus presented to the cell in the fluid flow.

Preferably, a diameter of each strut of the reticular structure is in the range of about 0.2 μm to about 10 μm, preferably in the range of about 0.5 μm to about 5 μm, more preferably in the range of about 1 μm to about 3 μm, most preferably in the range of about 1.5 μm to about 2.5 μm. In this respect, a diameter of a strut is understood to define the average extension/diameter of a cross section of the respective strut perpendicular to its longitudinal extension. Specifically, in case of a circular cross section, the diameter of the strut is understood as the diameter of said cross section. Otherwise, e.g. in case of an irregularly shaped cross section, the diameter of the strut may be the diameter of an area equivalent circle. This structure combines a efficient combination of high cell trapping reliability and minimum distraction of fluid flow.

It has turned out to be specifically preferred if a size of each window along its respective maximum extension is not more than about 90%, preferably not more than about 80%, more preferably not more than about 70%, most preferably not more than about two thirds of a diameter of the trapped cell and/or wherein a size of each window along its respective minimum extension is at least 10%, preferably at least 20%, more preferably at least 30%, most preferably at least one third of the diameter of the trapped cell to be trapped. Thus, specifically with regards to the device, is it preferred that a size of each window along its respective maximum extension is at most about 15 μm, preferably at most about 12 μm, more preferably at most about 10 μm, most preferably not more than about 8 μm and/or wherein a size of each window along its respective minimum extension is at least about 1 μm, preferably at least about 2 μm, more preferably at least about 5 μm, most preferably at least about 7 μm.

It is also preferred that the struts of the reticular structure of the at least one cell trapping element form at least 4 windows, more preferably at least 6, even more preferably at least 9, most preferably at least 12 windows, and/or preferably not more than 50, further preferably not more than 25, most preferably not more than 20 windows.

Preferably the reticular structure of the cell trapping element defines a concave cell receiving surface facing an incoming fluid flow, wherein a smallest extension of the concave cell receiving surface transverse to the fluid flow is at least about 1.1 times, preferably at least about 1.2 times, more preferably at least about 1.3 times, even more preferably at least about 1.4 times, most preferably at least about 1.5 times a diameter of the trapped cell. This ensures a quite reliable cell trapping and enhances that chance that a trapped cell remains trapped during a bioassay. Alternatively or additionally a smallest extension of the concave cell receiving surface transverse to the fluid flow is at most about 10 times, preferably at most about 5 times, more preferably at most about 3 times, most preferably at most about 2 times the diameter of the trapped cell. This ensures minimal impact on fluid flow (around the cell) and high selectivity to trap individual cell.

In a preferred embodiment, a gold layer may be provided to cover part of an inner surface of a microfluidic channel wall, wherein the reticular structure of cell trapping element is attached to the gold layer. This gold layer may thereby improve the stability of the mechanical attachment of the reticular structure to the microfluidic channel wall. Additionally, the gold layer may serve as an electrode for bioassay making use of the efficient immobilization of one or more cells, preferably a single cell.

Thus, in one aspect the present invention also provides a bioassay comprising the steps of a method of individually immobilizing one or more (single) cells under fluid flow conditions according to any one of the aspects described herein; and determining the kinetics of the binding of a ligand to the immobilized (single) cell(s).

Preferably, the bioassay comprises an optical excitation and/or an optical measurement (spectroscopic analysis, such as fluorescence spectroscopy), wherein light is emitted to or from a location in or at the trapped cell along a measurement light path transverse to the direction of fluid flow, and wherein the reticular structure has the shape of a segment of the surface of a general cylinder with a cylinder axis parallel to the measurement light path and with a concave face of said segment facing the incoming fluid flow.

Thus, in a preferred implementation of the device, the reticular structure has the shape of a segment of the surface of a general cylinder (or prism) with a cylinder axis parallel to the measurement light path and with a concave face of said segment facing the incoming fluid flow. In this respect, the “general cylinder” means a geometric shape which is defined as a surface consisting of all the points on all the lines which are parallel to a given line (e.g. the cylinder axis) and which pass through a fixed plane curve in a plane not parallel to the given line. In one example which may be implemented as a preferred embodiment, that fixed plane curve may be circle and the resulting cylinder may specifically be a circular cylinder. Specifically, the cylinder axis may be perpendicular to the plane of said fixed plane curve. However, the “general cylinder” is not limited to a circular cylinder. Instead, the reticular structure may also follow the shape of a segment of an elliptical cylinder surface or a segment of the surface of a prism, which may result from a polygonal fixed plane curve. Regardless of the actual details of the shape of the cylindrical segment, it is preferred that said segment has one concave side (e.g. the side facing the inner side of the cylinder) that faces the incoming fluid flow. Thereby, the concave face of the cylindrical surface supports an improved capability of capturing and holding a cell while maintaining the flow condition in the fluid. Specifically, if the fluid flow a rather laminar (and not too turbulent) the cell may sit quite stable inside the concave surface. Specifically, with the cylindrical axis being parallel to the light path, the cell can be stably held at an optical observation position on the light path, while at the same time the reticular structure does not mask up the observation position. Instead, the excitation and/or measurement light can be sent along the light path without being blocked by part of the reticular structure.

In one preferred embodiment of the present invention, the reticular structure is attached with one end (section) thereof (e.g. the lower end) to an inner surface of a first microfluidic channel wall (e.g. a bottom/base wall of the microfluidic channel). This attachment is sufficiently stable to keep this first end section connected even during the desired fluid flow conditions. In this preferred embodiment, the cell trapping element further comprises at least one support beam having a first end attached to another end (section) of the reticular structure (e.g. an upper end). A second end of the at least one support beam is attached to the inner surface of the first microfluidic channel wall at a position downstream relative to the position where the reticular structure is attached. Thereby, the support beam supports the second (e.g. upper) end section of the reticular structure so as to stabilize the whole reticular structure even under the desired fluid flow conditions.

In an alternative implementation, the reticular structure is attached with one end (section) thereof (e.g. the lower end) to an inner surface of a first microfluidic channel wall, such as a bottom wall (base wall), and with another end (section) thereof (e.g. an upper end) to an inner surface of a second microfluidic channel wall, such as a top wall (cover) of the microfluidic channel substantially opposite to the first microfluidic channel wall. Thereby, each of opposite end sections of the reticular structure can be stable held at opposite walls of the microfluidic channel, thereby ensuring a high stability of the whole cell trapping element even under the desired fluid flow conditions. Preferably, the reticular structure of the cell trapping element is compressed between inner surfaces of the first and second microfluidic channel wall. Specifically, the reticular structure can be initially manufactured with a height that is larger than the height of the microfluidic channel (i.e. the distance between first and second microfluidic channel walls) before said opposing microfluidic channel walls are assembled, so that the reticular structure is clamped between these channel walls (e.g. the bottom and top surfaces of said channel.

Specifically, the height of the reticular structure may initially be 10% to 30% larger than the height of the microfluidic channel.

Typical cell diameters for eukaryotic cells may range, dependent on the particular type of cell, in the region of 10 to 20 μm. However, some eukaryotic cells, e.g. yeasts or erythrocytes, can be smaller down to a few μm, and certain cell types are larger, e.g. human oocytes (typically 120 μm) or plant cells, which can extend over several 100 μm. Furthermore, prokaryotic cells can be between a few μm to as small as having a diameter below 1 μm. In this context, the type of cell to be immobilized in the methods of the present invention is not particularly limited in any way, including prokaryotic and eukaryotic cells of any kind.

Typical absolute values for a diameter of the half-cylindrical reticular structure may be in the range of 10 to 30 μm. However, depending on the type of cell to be immobilized, said diameter can range from 1 to 250 μm.

Preferably, the microfluidic channel has a substantially rectangular cross section transverse to the (main) fluid flow direction. In that respect, preferred values for a height of the microfluidic channel range from about 30 μm to about 75 μm. Moreover, preferred values for a width of the microfluidic channel range from about 500 μm to about 1000 μm, e.g. about 750 μm. Specifically, depending on the type of cells that should be immobilized, the height of the microfluidic channel may even be larger than 100 μm and may even extend over several 100 μm. Such relatively large channel heights may be specifically desirable if human oocytes of plant cells are to be trapped, for example. In some embodiments, it is preferred even for such (relatively) large channel heights that the reticular structure extends over the whole height of the microfluidic channel, so that the reticular structure can be supported by the channel walls opposing in height direction. Moreover, in cases with a substantially generally cylindrical shape of the reticular structure having the cylinder axis extending substantially in height direction, the extension of the reticular structure over the whole height can ensure that a trapped cell does not easily escape along the cylinder axis at one (open) end of the reticular structure, without requiring to provide a strut structure at such an open end as an additional barrier for the cell. Avoiding such a strut barrier specifically ensure to avoid masking excitation and/or measurement light that can be sent substantially parallel to the height direction and/or the cylinder axis.

A large channel height, optionally even combined with an analogously large extension of the reticular structure in height direction, can even be advantages in cases where (relatively) small cells are to be immobilized. Even if the reticular structure is adapted in width direction (i.e. transvers to the direction fluid flow and perpendicular to the height direction), e.g. the direction of the smallest extension transverse to the fluid flow, in accordance with the diameter of the cells to be immobilized as described above, the reticular structure may extend in height direction over the whole height of the microfluidic channel. Thus, in some preferred embodiments, the reticular structure may be multiple times higher than wide. In these embodiments, the limited extension of the reticular structure in width direction can ensure a high selectivity in trapping (single) cells of a specific size, while the relatively large extension of the reticular structure in height direction may allow to hold multiple identical cells, preferably aligned along an axis that may be used as an optical axis for excitation and/or measurement light. This can be specifically advantages with regards to a high response sensitivity for bioassays in which a physiological response of the immobilized cells is triggered, and said response, e.g. the release of a certain factor, is measured with the help of a biosensor in the immediate vicinity of the immobilized cells, or a biosensor lying downstream of the immobilized cells.

In some embodiments it is preferred that the cell trapping element comprises a support structure such as the support beam described herein, even if the reticular structure extends over the whole height of the microfluidic channel and even if the reticular structure is supported by the walls of the microfluidic channel opposing in height direction. This is specifically advantageous for the mechanical stability of the reticular structures even in high flow velocities in cases of a high aspect ratios between the height and the width of the reticular structure, e.g. if the reticular structure is at least 5 times or even at least 10 times higher than wide.

In specific embodiments, the diameter of each strut of the reticular structure is 1.5 to 2.5 μm, preferably 1.6 to 2 μm, more preferably 1.7 to 1.9 μm, e.g. about 1.8 μm.

The reticular structures used in the methods of the present invention comprising rectangular windows (or meshes). Preferably, the length of the larger side of said rectangular windows is at most two thirds of the diameter of the cells to be trapped, and the length of the smaller side of said rectangular windows is at least one third of the diameter of the cells to be trapped.

In absolute values, the length of the larger side of said rectangular windows is preferably between 5 and 15 μm, and the length of the smaller side of said rectangular windows is preferably between 2 μm and 7 μm. However, depending on the size of the cells to be trapped, the larger side of said rectangular windows can be between 0.6 to 100 μm, and the length of the smaller side of said rectangular windows is preferably between 0.3 μm and 50 μm.

The reticular structures to be used in the methods of the present invention can be fabricated by photon-stimulated polymerization, such as 2-photon polymerization (2PP) as known in the art. Accordingly, the material said structures are made of include suitable photopolymers, such as negative tone IP-Dip or IP-Visio photoresigns, SU8, positive tone photopolymers and hydrogels.

The bottom surface of the microfluidic channel used in the methods of the present invention, i.e., the surface on which the reticular structures are adhered, are not particularly limited and include any surfaces on which respective structures can be fabricated by 2PP. Suitable materials in this respect include glass, silicon, metals (e.g. gold and/or chrome), ceramics and/or polymers such as polydimethylsiloxane (PDMS), polypropylene (PP) and/or SU8. In preferred embodiments, the bottom surface of the microfluidic channel, and/or the top surface of said channel, are made of an optically transparent material, e.g. glass, in order to allow for microscopic, e.g. fluorescence microscopic, observation and/or analysis of the immobilized cells.

Means for actually immobilizing cells using the methods of the present invention are not particularly limited and are known in the art. They include any means of loading the respective microfluidic channel/microfluidic device with a fluid containing cells. Suitable fluids include any suitable buffers and media which allow the suspension of cells in the microfluidic flow. These can be of natural (e.g. serum, blood, amniotic fluid) or artificial source or mixes thereof. Artificial fluids include buffered salt solutions such as phosphate buffered saline (PBS) or culture media which keeps the pH of the cell suspension stable while supplying required nutrients, e.g. the basic medium MEM or the more complex medium RPMI-1640.

The cell density of a respective fluid used to load the microfluidic channel/microfluidic device with cells can be in the range of 0.1-$10^6$ cells/ml. Lower cell concentrations are possible as well with respectively longer loading times or additional guiding structures towards the (single) cell traps to enhance the probability of the cell entering the trap. In a preferred embodiment, the guiding structure(s) may comprise a mesh wall extending substantially from bottom to top of the microfluidic channel such that it allows substantially unrestricted buffer flow while it guides any incoming cell towards the reticular structure of the cell trapping element. Thereby, cells which would have passed by the trap in a channel that is broader than the reticular structure of the cell trapping element are forced to enter the trap first and only surplus cells will pass the filled trap. This can ensure a considerable improvement of the cell trapping efficiency. In order to ensure passage of surplus cells, it is preferred that a gap is provided between the guiding structure and the reticular structure of the cell trapping element, which is larger than the diameter of the cells to be trapped.

The microfluidic devices of the present invention can comprise one or more of the cell trapping elements, each including a reticular structure. In cases where more than one cell trapping elements is present, they are preferably arranged so that the distances therebetween are at least not smaller than the size of the cell trapping elements (i.e. their extension in the direction of the distance therebetween). This ensure a limited distortion of the fluid flow and avoids blockade of cell flow at undesired positions between the cell trapping elements. Furthermore, in case of more than one cell trapping elements being arranged in multiple rows with respect to the direction of fluid flow, the respective structures in different rows are preferably arranged in an offset manner with respect to the different rows.

In preferred embodiments, the methods of the present invention are performed in vitro, i.e., they are not performed on the human or animal body.

As used herein, the term “about” is intended to be a modifier of the specified value of ±10%, preferably ±9%, ±8%, ±7%, ±6%, ±5%, ±4%, ±3%, ±2%, or ±1%. By way of example, the term “about 10 μm” is intended to encompass the ranges of 9 to 11 μm, preferably 9.1 to 10.9 μm, 9.2 to 10.8 μm, 9.3 to 10.7 μm, 9.4 to 10.6 μm, 9.5 to 10.5 μm, 9.6 to 10.4 μm, 9.7 to 10.3 μm, 9.8 to 10.2 μm, or 9.9 to 10.1 μm.

In the present invention, as a first requirement for immobilizing both adherent and suspension cells non-specifically, a mechanical trap system was focused on. First trap designs by photolithography included solid pillar structures. These pillar arrangements enable to stop cells in a microfluidic flow. However, they are quickly filled up by many cells which results in a total block of buffer flow, preventing any controlled kinetic experiment on top of the captured cells. Thus, a requirement for the trap being made up of a mesh structure was identified, and the reticular structures of the present invention realized as an ideal mechanical cell trap system.

In particular, the present in invention provides robust (single) cell traps fabricated in a microfluidic channel preferably by two-photon polymerization (2PP) that withstand a very high average flow velocity of 1 m/s or more. The traps may be manufacture by a direct laser written thin reticular structure allowing a good flow around the captured cells as well as optical measurements. Therefore, they enable the characterization of binding kinetics between active substances and cells. Preferably, the traps may have the shape of half a circular cylinder and capture the cells hydrodynamically.

Figure 1B:
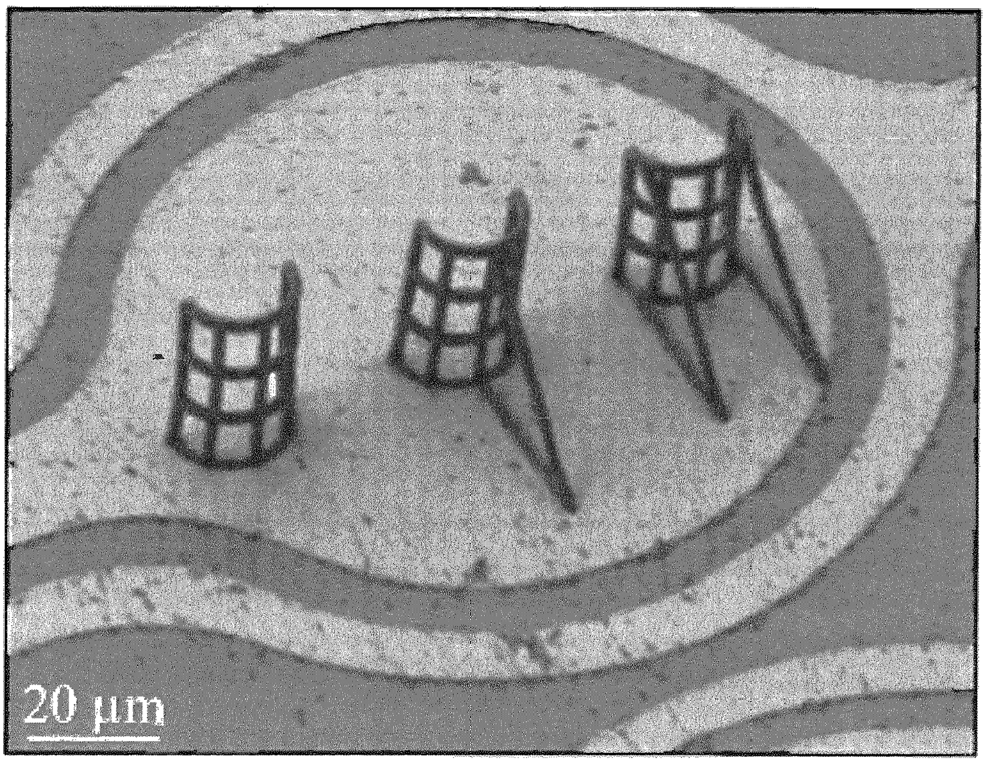
Figure 2:
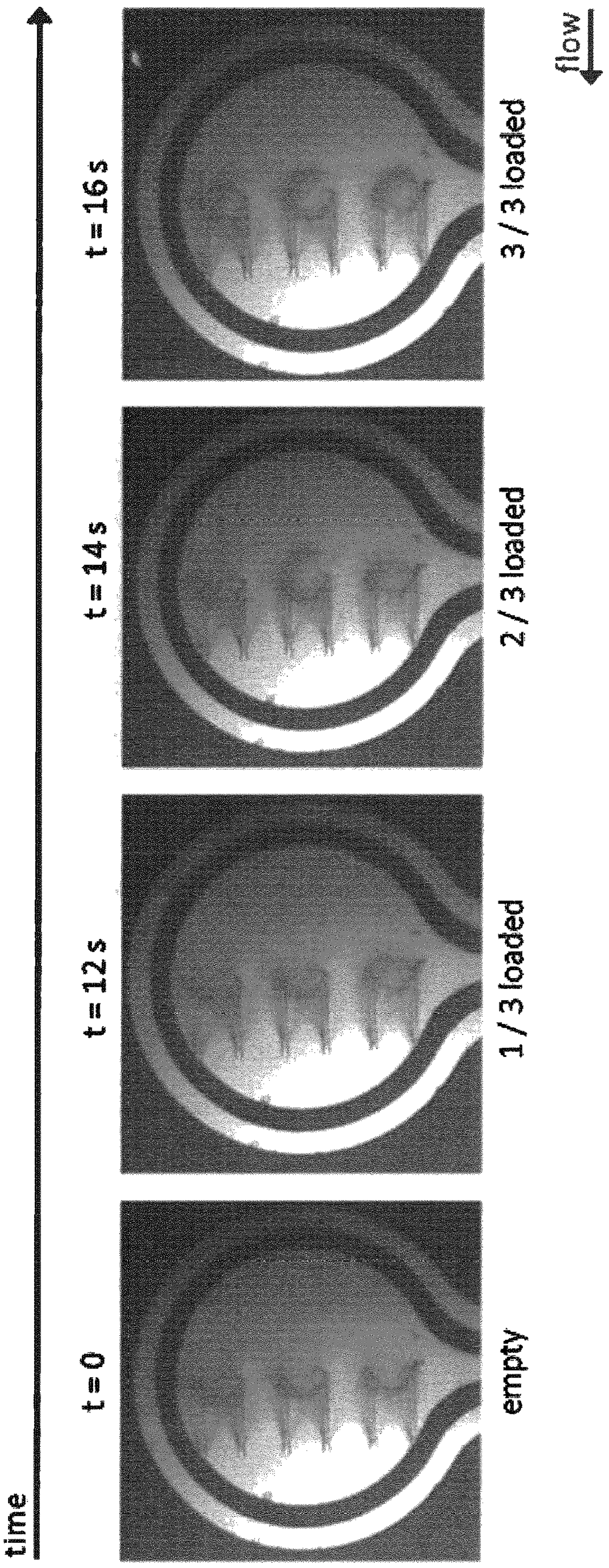
Figure 3A:
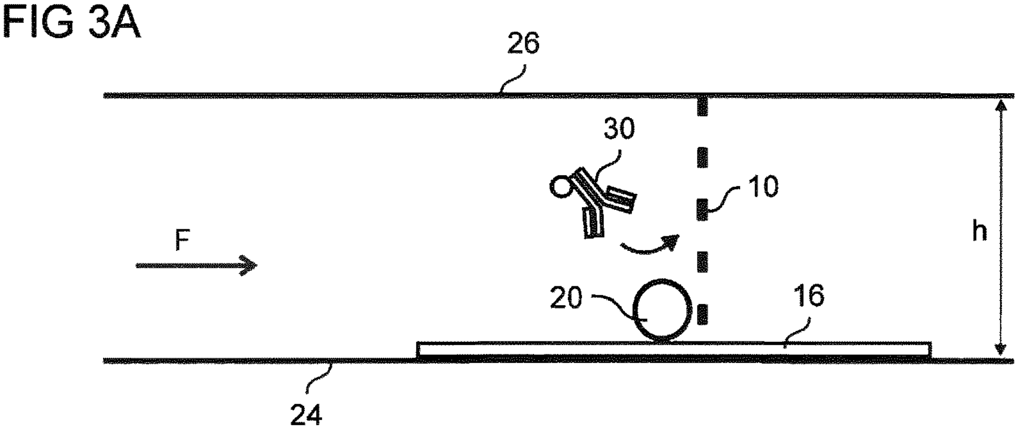
Figure 3B:
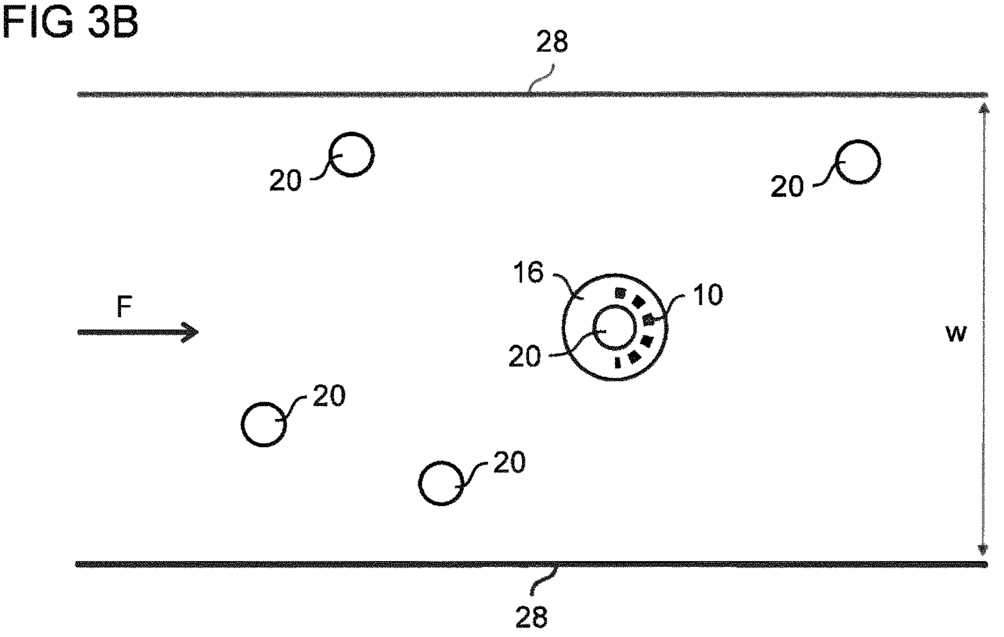
Figure 3C:
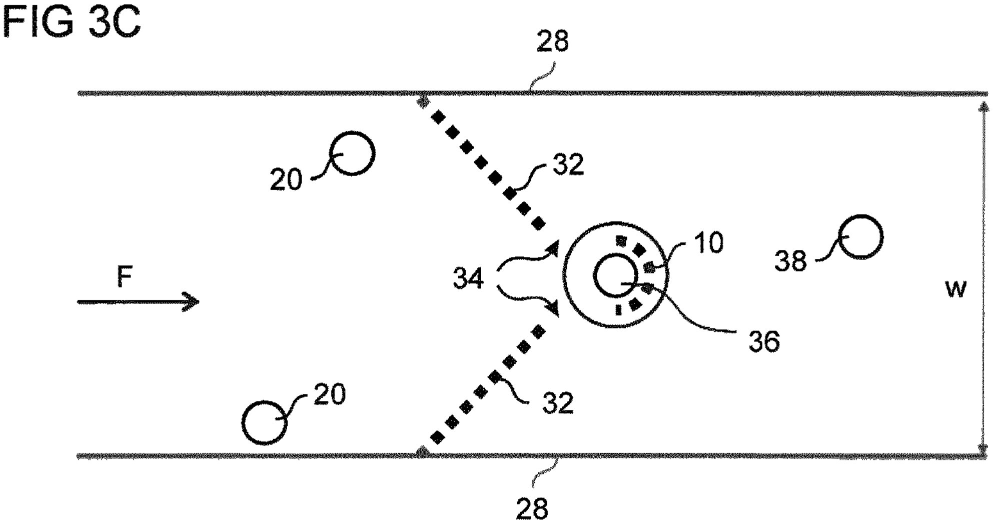
Figure 4:
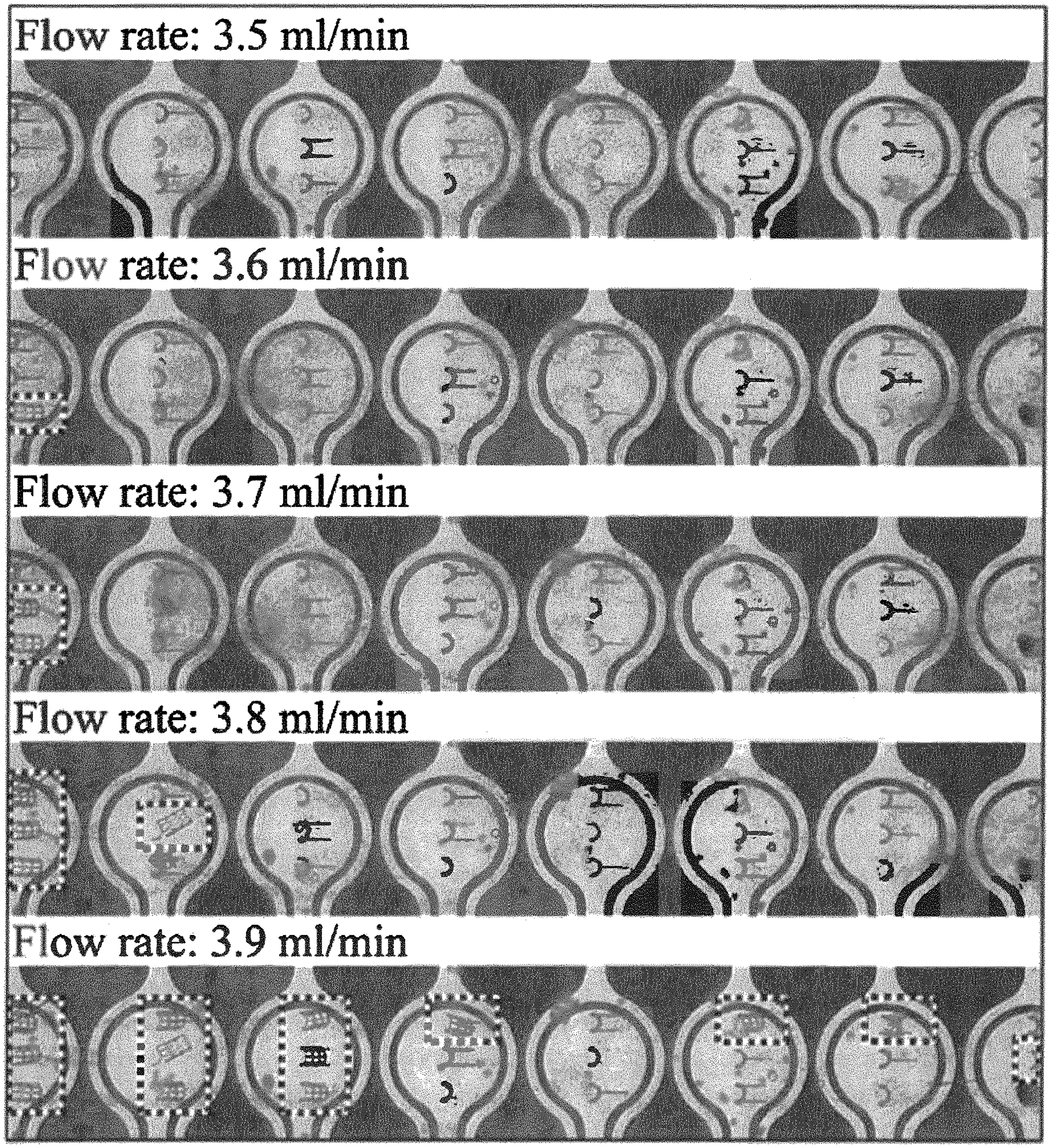
Figure 5:
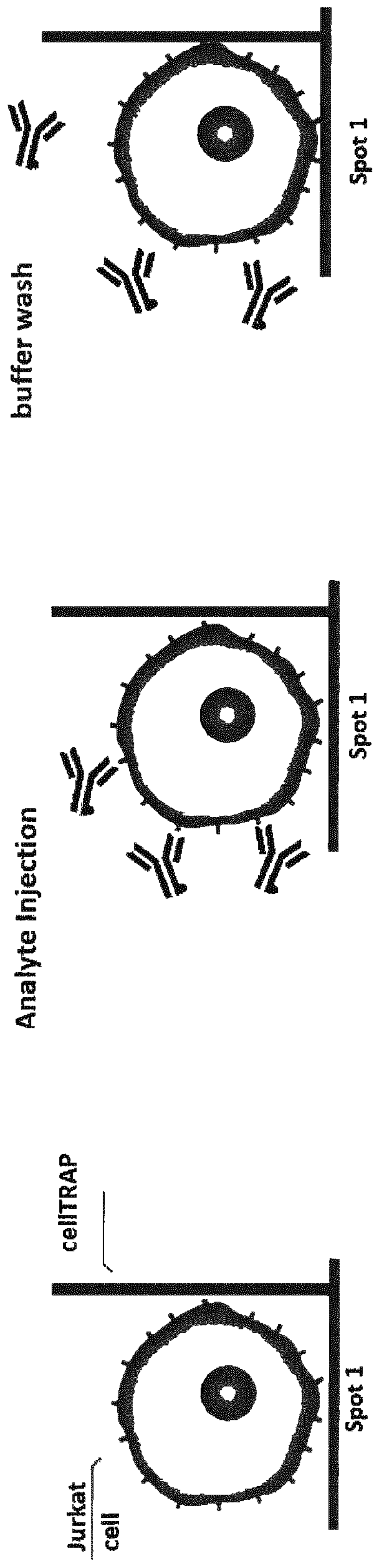
Figure 6:
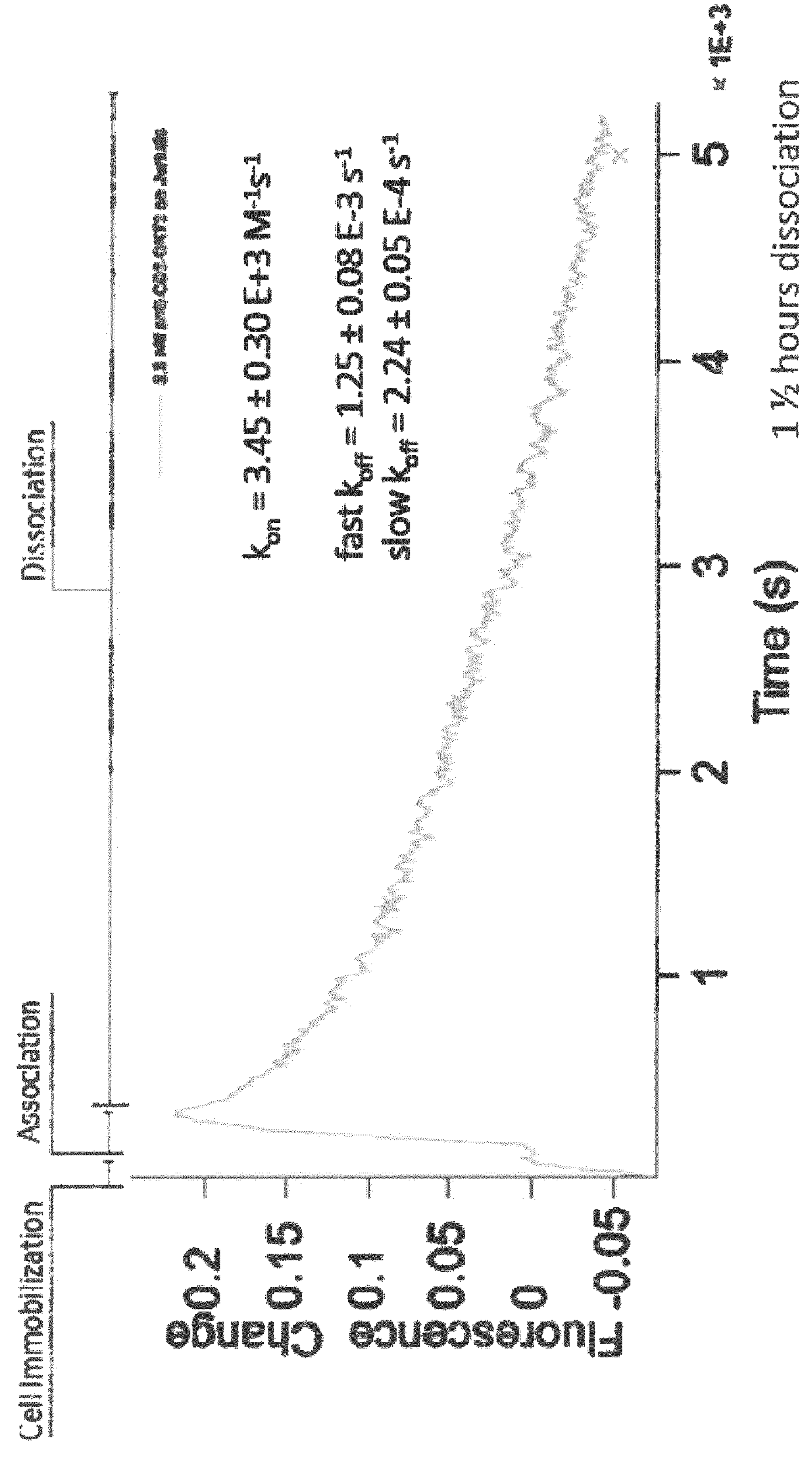

Further details and advantages for preferred embodiments of the present invention will be described with reference the attached figures, which show:

FIG. 1A a schematic view a various cell trapping elements that may be implemented in preferred embodiments of the present invention;

FIG. 1B an SEM (scanning electron microscope) image of the different traps from FIG. 1A;

FIG. 2 time-resolved trapping of Jurkat cells in a device according to a preferred embodiment of the present invention;

FIG. 3 a side view (FIG. 3A) and a top view (FIG. 3B) of schematic cross section of a device in operation according to a preferred embodiment of the present invention; FIG. 3C is a top view of an alternative embodiment with an additional guiding structure included;

FIG. 4 photographic top view of 24 cell traps at increasing flow rates;

FIG. 5 schematic stages of cell trapping, association measurement, and dissociation measurement;

FIG. 6 measurement results of kinetic rates for association and dissociation on a captured cell.

FIG. 1A represents a sketch of three different cell trapping elements 10 according to different preferred embodiments of the present invention. All three cell trapping elements 10 are arranged on a metal (gold) plate, which may cover part of an inner surface of a microfluidic channel. The flow direction of the desired fluid flow is indicated with arrow F in FIG. 1A. In the examples of FIG. 1A, each of the cell trapping elements 10 comprises a reticular structure made of horizontal struts 12 and vertical struts 14. While the vertical struts 14 rise straight up from the gold layer to about 35 μm in this example, the horizontal struts 12 form bent arcs, close to circular arcs in this example, which are substantially parallel to the gold layer at various distances therefrom. The vertical and horizontal struts are fixedly connected to each other at their respective crossings. In that manner, for each of the reticular structures of the respective cell trapping element 10, there vertical and horizontal struts are is preferable formed integrally with each other as a single piece. This ensure high mechanical stability of the reticular structure, and it can be achieved by 2-photon polymerization (2PP), for example In the examples of FIG. 1A, the (roughly) circular arcs of the horizontal struts 12 have a diameter of about 20 μm. The diameter of each strut of the grid is about 1.8 μm. This thickness turned out to ensure sufficient stability to suppress or avoid undesired deformations. The meshes (windows/openings 18) have a size of about 6 μm by 8 μm, preventing the cells from passing through the trap. The gold layer 16 as base improves the adhesion of the 2PP structure and enables the interface finding in the Photonic Professional GT.

While the left most cell trapping element in FIG. 1A basically consists of the reticular structure only, the middle and the right cell trapping element additional comprise at least one support beam 22, which supports an open end of the reticular structure. More specifically, while the lower end section of the respective reticular structure is attached to the gold layer 16, in the middle and the right cell trapping element 10 of FIG. 1A, the upper end is supported with one additional support beam 22 (middle) or even two additional support beams 22 (right). While each support beam 22 is attached with a first end thereof to an upper end section of the respective reticular structure, the second end of each support beam is attached to the gold layer 16 at a position downstream from the position of the reticular structure.

The shape of the reticular structures with a substantially circular cylindric shape corresponding to a half-circular base was designed such as to well accommodate a spherical cell. A mesh-like structure was chosen as trap wall to allow unrestricted buffer passage. The windows 18 in the trap wall allow flow to pass through the traps and do not divert flow sideways. The window size was optimized to stop cells of >10 μm diameter in flow but allow smaller cell fragments to pass through and not clutter the trap. A good window size for ~15 μm large Jurkat cells is 6×8 μm.

Structures of this size and complexity cannot be produced with standard photolithography methods. Therefore, the 2PP method was chosen for direct laser writing of the cell traps in an IP-Dip polymer with a Photonic Professional GT (Nanoscribe GmbH) (FIG. 1B). Traps can be structured both on glass or on top of sensors such as a gold layer, which is pre-structured on a glass chip. FIG. 1B shows an SEM (scanning electron microscope) image of the different traps on a reused chip. The traps protrude from the chip as designed in FIG. 1A. A slight shrinkage can be noticed at the upper part of the left trap.

Initial tests showed possible flow-dependent instability of the traps. Therefore, to increase the stability, the height of traps was designed to be slightly more than the channel height, which is leading to clamping of the trap between top and bottom cover slip of the biosensor chip as will be illustrated in more detail in connection with FIG. 3 further below.

FIG. 2 illustrate time-resolved trapping of Jurkat cells in a switchSENSE instrument. Specifically, the cells are collected in the concave side of the trap. Traps open on top are clamped between upper and lower cover slip of the biochip to enhance stability and prevent cells from passing over the trap.

FIGS. 3A and 3B show an application of the cell traps according to the present invention in a microfluidic channel, wherein single cells 20 may be captured and fluorescence-labeled antibodies 30 added to the system. Specifically, FIG. 3A shows a side view and FIG. 3B a top view of an application of cell traps in a microfluidic channel. A small trap 10 made from a mesh structure, with dimensions fitting to a single cell 20, is placed onto a gold electrode 16. This design captures a single cell 20 only and allows single-cell analysis, e.g. binding kinetics of fluorescently labeled antibodies to cell surface markers. (Figure not drawn to scale). In order to stabilize the cell trapping element 10 in this embodiment, the reticular structure thereof is clamped between a bottom wall 24 and a top wall (cover) 26 of the microfluidic channel. This can be achieve by initially manufacturing the reticular structure (on the bottom wall 24 or the gold layer 16) to a height of about 5% to about 20% higher than a finite channel height h and subsequently compressing it (when adding the cover 26) to the channel height h. A similar situation is schematically shown from a top view in FIG. 3B, where the curved cross section of the cell trapping element 10 can be seen. The channel width w between side walls 28 is also schematically depicted.

In order to test the influence of support structures on the stability of the cell traps according to the present invention at different flow rates, cell traps having no, one, or two stabilizer bars extending from the top backside of the reticular structure to the surface of the bottom surface of the microfluidic channel in the direction of fluid flow, forming an angle with said bottom surface of about 45° were generated. FIG. 3C show a schematic top view of another preferred embodiment, which comprises a guiding structure 32. The guiding structure may be implemented as another reticular structure (mesh structure), which preferably extends over the whole height between the bottom wall 24 and the top wall 26. It may also be attached to or arranged with one end at one of the side walls 28, respectively. From said side wall 28 towards the center of the microfluidic channel the guiding structure 32 preferably extends downstream the fluid flow direction, such that cells are guided toward the center of the microfluidic channel. In the embodiment shown in FIG. 3C, two guiding structures 32 are shown, which form a pair of guiding structures, both guiding cells towards a common cell trapping element 10, which may be arranged substantially in the center of the microfluidic channel. In other preferred embodiments there may be only one guiding structure or even multiple pairs of guiding structures 32, which are preferably arranged in a zigzag pattern, where each pair of guiding structures guides the cells towards a common cell trapping element.

As shown in FIG. 3C, a gap 34 formed between the guiding structures 32 and the cell trapping element 10 allows cell to escape, if the cell trapping element is already loaded with a trapped cell 36. In this case surplus cells 38 can simply pass through the gap 34 in order to avoid a blockade of the microfluidic channel device.

FIG. 4 shows photographs of 24 cell traps in one 75 μm high channel from the top at increasing flow rates. The broken traps are marked with black/white dotted rectangles. As can be taken from FIG. 4, up to a flow rate of 3.5 ml/min (corresponding to a velocity of about 1 m/s in the respective setup) all traps are intact. At higher flow rates the first traps start breaking. At a flow rate of 3.9 ml/min (corresponding to about 1.1 m/s) half of the traps are broken. The different support structures show no effect on the stability. Instead mostly the first traps in the flow break probably because they are exposed to the highest flow velocity.

FIG. 5 shows a schematic representation of three subsequent stages during a bioassay. In a first stage, an individual cell is trapped by means of a cell trapping element at a predetermined location (spot 1). In a next stage, fluorescently labeled analyte (e.g. antibody, MHC complex, or any other fluorescently-labeled molecule) is injected for association measurement. The analytes include fluorescent marker to allow detection of the association process and the specifically the association rate. In a third stage, buffer fluid is intended for dissociation measurement, where the analyte dissociates from the cell again. Specifically, accuracy of the measurement in the phase of association and the phase of dissociation turned out to be critically depend on a flow rate or the fluid velocity at the location of the trapped cell. In case of low flow rates (or low fluid velocity) during the association phase, the measurement of the association rate would rather be dominated by mass transport limitation than by the actual association dynamics. In case of low flow rates (or low fluid velocities) during the dissociation phase, the measurement of the dissociation rate would be adulterated by rebinding effects of the analytes to the cell.

FIG. 6 shows intensity of fluorescence measurement during the three stages illustrated in FIG. 5. Specifically, the measurement starts with the cell immobilization followed by the stage of association and finally the stage of dissociation. The presented highly precise and reproducible measurements were achieved with controlled trapping and measurement of individual cells (i.e. one single cell per cell trapping element at the same time) and at least with fluid velocities in the ranges of about 50 mm/s to about 100 mm/s, which have not been reliably available with conventional cell immobilization concepts. In the example of FIG. 6, the high precision of the measurement even allows to distinguish between two overlayed dissociation processes have different decay constants "fast $k_{off}$" and "slow $k_{off}$". While the coefficient "fast $k_{off}$" can be assigned to a 1-arm binding of the analyte to the cell (also called affinity), the coefficient "slow $k_{off}$" can reflect the dissociation rate for a 2-arm binding of the analyte to the cell (also called avidity). Such deep insight into the specific binding and dissociation mechanisms is a powerful tool for improving judgment of efficacy and safety of drugs.

LIST OF REFERENCE NUMBERS

10 cell trapping element
12, 14 strut
16 metal (gold) plate/layer
18 window/opening
20 cell
22 support beam
24 bottom wall/base wall
26 top wall/cover
28 side wall
30 fluorescence-labeled antibody
32 guiding structure
34 gap
36 trapped cell
38 surplus cell
F fluid flow (direction)
h channel height
W channel width

The invention claimed is:

1. A method for immobilizing cells under fluid flow conditions during a bioassay, the method comprising:

flowing a fluid that includes cells in a fluid flow direction through a microfluidic channel of a microfluidic device; and trapping at least one of the cells with a cell trapping element arranged in the microfluidic channel, the cell trapping element including a reticular structure, a portion of the reticular structure extending in a second direction transverse to the fluid flow direction, the reticular structure including a plurality of struts defining a plurality of windows, the windows trapping the cells during flowing of the fluid through the cell trapping element, wherein the reticular structure includes a concave cell receiving surface through which the fluid flows.

2. The method of claim 1, wherein a velocity of the fluid flowing through the windows of the cell trapping element is at least 1 mm/s.

3. The method of claim 1, wherein a size of each window along its respective maximum extension is not more than 90% of a diameter of the trapped cell.

4. The method of claim 1, wherein a smallest extension of the concave cell receiving surface is at least 1.1 times a diameter of the trapped cell, and wherein a smallest extension of the concave cell receiving surface transverse to the fluid flow is at most 10 times the diameter of the trapped cell.

5. A method of performing a bioassay, the method comprising:

the method for immobilizing the cells according to claim 1; and determining kinetics of binding of a ligand to the trapped cell.

6. The bioassay of claim 5, comprising an optical excitation and an optical measurement, wherein light is emitted to or from a location in or at the trapped cell along a measurement light path transverse to the direction of fluid flow, and wherein the concave cell receiving surface of the reticular structure has a shape of a segment of a surface of a general cylinder with a cylinder axis parallel to the measurement light path and with a concave face of the segment facing the flowing fluid.

7. A microfluidic device for immobilizing cells under fluid flow conditions during a bioassay, the microfluidic device comprising a microfluidic channel configured to direct fluid flow in a fluid flow direction; and a cell trapping element arranged in the microfluidic channel, the cell trapping element including a reticular structure, a portion of the reticular structure extending in transverse to the fluid flow direction, the reticular structure including a plurality of struts defining a plurality of windows, the windows configured to trap the cells during flowing of the fluid through the cell trapping element, wherein the reticular structure includes a concave cell receiving surface configured to permit the fluid to flow therethrough.

8. The device of claim 7, wherein a diameter of each strut of the reticular structure is in a range of 0.2 μm to 10 μm.

9. The device of claim 7, wherein a size of each window along its respective maximum extension is at most 15 μm, and wherein a size of each window along its respective minimum extension is at least 1 μm.

10. The device of claim 7, further comprising a gold layer covering part of an inner surface of a wall of the microfluidic channel, wherein the reticular structure is attached to the gold layer.

11. The device of claim 7, wherein the concave cell receiving surface of the reticular structure has a shape of a segment of a surface of a general cylinder with a cylinder axis parallel to a measurement light path and with a concave face of the segment configured to face incoming fluid flow.

12. The device of claim 7, wherein the microfluidic channel has a cross section transverse to the direction of the fluid flow in a range of $0.2 \cdot 10^4$ $\mu m^2$ to $20 \cdot 10^4$ $\mu m^2$.

13. The device of claim 7, wherein the reticular structure is attached with one end thereof to an inner surface of a first microfluidic channel wall, and wherein the cell trapping element further comprises at least one support beam having a first end attached to another end of the reticular structure and having a second end attached to the inner surface of the first microfluidic channel wall at a position downstream relative to the position where the reticular structure is attached.

14. The device of claim 7, wherein the reticular structure is attached with one end thereof to an inner surface of a first microfluidic channel wall and with another end thereof to an inner surface of a second microfluidic channel wall substantially opposite to the first microfluidic channel wall.

15. The device of claim 14, wherein the reticular structure of the cell trapping element is compressed between inner surfaces of the first and second microfluidic channel wall.

16. The device of claim 7, wherein a diameter of each strut of the reticular structure is in a range of 1.5 μm to 2.5 μm.

17. The device of claim 7, wherein a size of each window along its respective maximum extension is not more than 8 μm, and wherein a size of each window along its respective minimum extension is at least 7 μm.

18. The device of claim 7, wherein the microfluidic channel has a cross section transverse to the fluid flow direction in a range of $1 \cdot 10^4$ $\mu m^2$ to $5 \cdot 10^4$ $\mu m^2$.

* * * * *